United States Patent [19]

Vaillancourt

[11] 4,205,675
[45] Jun. 3, 1980

[54] CATHETER PLACEMENT UNIT WITH NEEDLE REMOVAL PROVISION AND METHOD OF USE

[75] Inventor: Vincent L. Vaillancourt, Livingston, N.J.

[73] Assignee: Johnson & Johnson, N.J.

[21] Appl. No.: 915,636

[22] Filed: Jun. 15, 1978

[51] Int. Cl.² .................. A61M 5/00; A61M 25/00
[52] U.S. Cl. .................. 128/214.4; 128/DIG. 16; 128/348
[58] Field of Search ............ 128/214.4, 221, 348, 128/347, DIG. 16

[56] References Cited

U.S. PATENT DOCUMENTS

| | | | |
|---|---|---|---|
| 3,055,361 | 9/1962 | Ballard | 128/214.4 |
| 3,220,411 | 11/1965 | Czorny | 128/214.4 |
| 3,225,762 | 12/1965 | Guttman | 128/214.4 |
| 3,314,427 | 4/1967 | Stafford | 128/214.4 |
| 3,599,637 | 8/1971 | Schwartz | 128/214.4 |
| 3,739,778 | 6/1973 | Monestere et al. | 128/214.4 |
| 3,757,771 | 9/1973 | Ruegg et al. | 128/214.4 |
| 3,825,001 | 7/1974 | Bennet et al. | 128/214.4 |
| 3,851,647 | 12/1974 | Vaillancourt et al. | 128/214.4 |
| 4,037,600 | 7/1977 | Poncy et al. | 128/214.4 |

FOREIGN PATENT DOCUMENTS 1,534,119  6/1968  France .................... 128/214.4

*Primary Examiner*—Dalton L. Truluck
*Attorney, Agent, or Firm*—Donal B. Tobin

[57] ABSTRACT

A catheter placement unit for use with an introducer needle and an introducer catheter including a hollow tube and a fitting at one of its ends. The placement unit comprises a connector having an internal bore and including a male fitting member for mating with the catheter fitting to provide a connection. A protective sheath is secured to the connector and it includes a hole, closable elastic member or the like in its periphery for allowing insertion of the needle therethrough and into the bore of the connector. A length of flexible, hollow catheter tubing is movably positioned within and enclosed by the sheath.

A method of placing a catheter into a patient includes the steps of mating a connector of a catheter placement unit, substantially as described above, to a fitting on an introducer catheter. A needle is inserted through the periphery of the sheath and through the connector into the lumen of the introducer catheter so that the tip of the needle extends slightly beyond its end. The introducer catheter and needle are inserted into a patient. While leaving the introducer catheter in position in the patient, the needle is withdrawn from the unit. With the flexible hollow tubing still enclosed by the sheath, it is manipulated internally through the connector and the introducer catheter and then into the patient.

15 Claims, 7 Drawing Figures

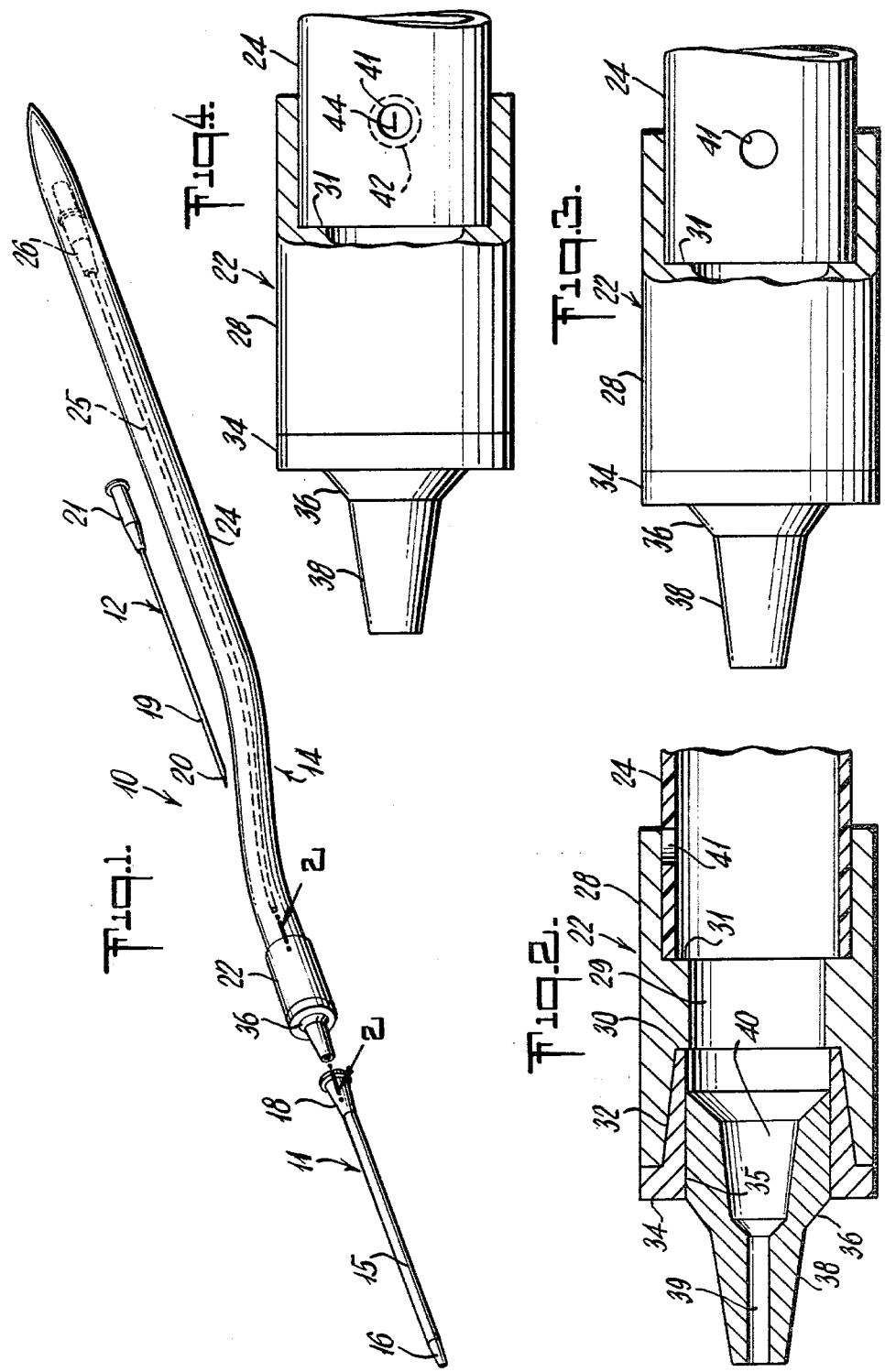

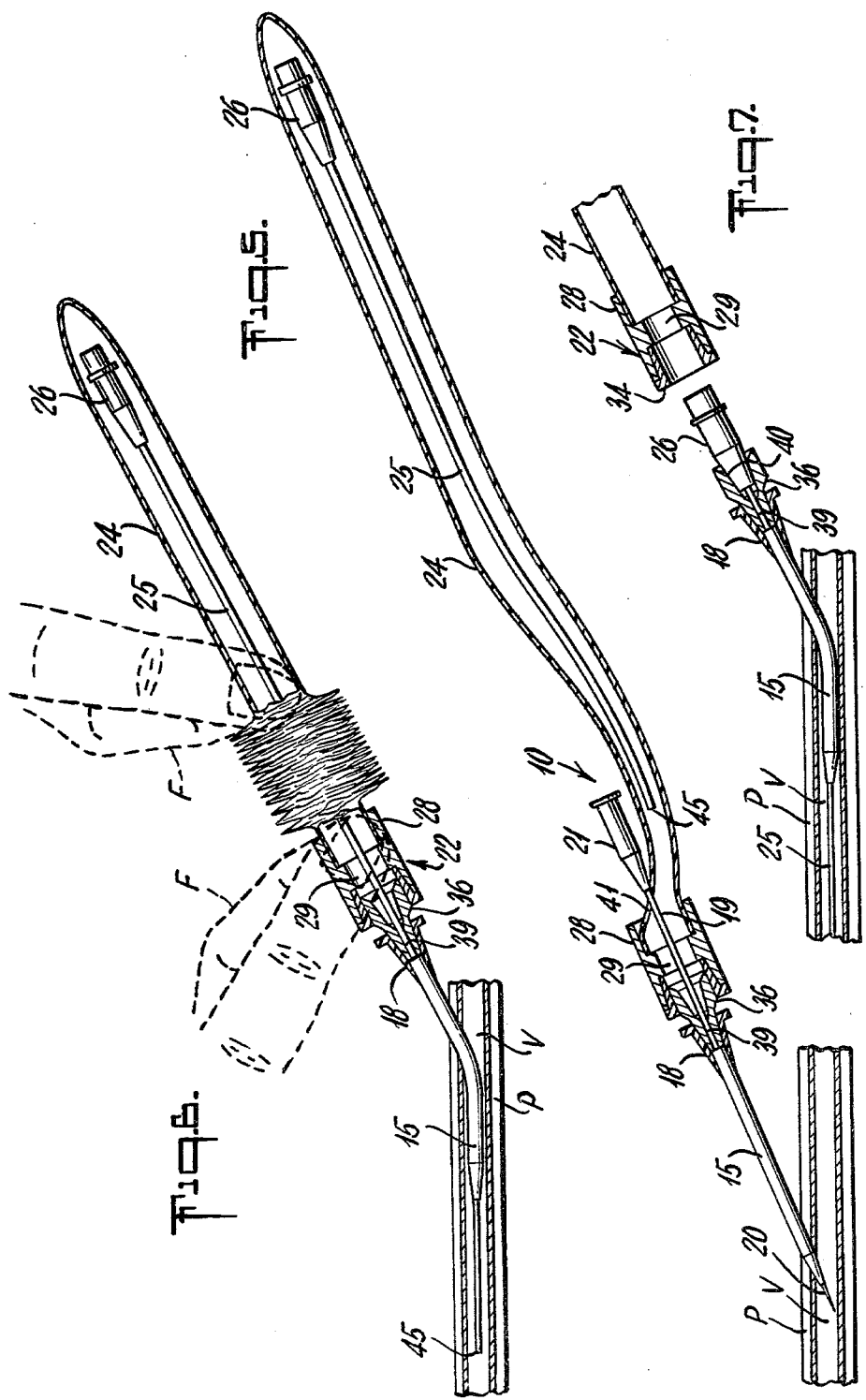

CATHETER PLACEMENT UNIT WITH NEEDLE REMOVAL PROVISION AND METHOD OF USE

BACKGROUND OF THE INVENTION

The present invention relates to a catheter placement unit suitable for insertion into the blood system and other body tissue of a patient, and also concerns a placement system for inserting the catheter into a patient and its method of use.

Catheters having a generally elongate axial dimension are utilized in intravenous therapy for a number of purposes including delivery of intravenous liquid and pressure monitoring services. These catheters are normally introduced into the patient's vein at an extremity and threaded to a major vein, or ultimately, to the heart. In this regard, the central venous pressure may be readily measured and monitored with compatible equipment. Introduction of the catheter into the patient generally poses the area of difficulty when using a device of this type.

Prior catheter placement units or systems have used a metal introducer needle for venipuncture purposes and also to provide a passage for the catheter into the venous system. Many prior systems, however, have been designed to leave the introducer needle in position in the patient's vein while the extended catheter is slidably pushed through the needle and then into the patient. Catheter devices of this type are typified in U.S. Pat. Nos. 3,314,427 and 3,055,361. One of the problems associated with this technique is the danger of the catheter, generally made of flexible plastic, being cut or severed as it passes the extremely sharp point on the needle.

Other catheter placement units have been proposed which have recognized the inherent problems of leaving the introducer needle in the patient during catheter use and have therefore provided for removal of the needle. One technique has been to use an introducer catheter with the needle, but without the extended catheter being attached during venipuncture. After venipuncture, the needle is withdrawn, leaving the introducer catheter inserted in the patient's vein. This, of course, introduces another problem, namely, blood escaping from the patient's vein through the intravenous catheter. Accordingly, these catheter placement devices have had to provide some means of preventing the escape of blood, either by using a seal on the catheter device or the application of digital pressure above the insertion site, or some combination thereof. As soon as the introducer needle is withdrawn, the catheter is then generally connected to the introducer catheter whereupon it is slidably inserted through the catheter and then into the patient's vein. Devices of this type are typified in U.S. Pat. Nos. 3,825,001 and 3,757,771. It can be seen, that these type catheter units which provide for the removal for the needle are not "closed systems." In other words, the catheter is not attached to the introducer needle-introducer catheter combination upon original insertion into the patient; such attachment is only made after the needle is withdrawn. Accordingly, the need for further improvements is recognized in the utilization of catheter placement units and their introduction into a patient.

SUMMARY OF THE INVENTION

A catheter placement unit of the present invention is intended for use with an introducer needle and an introducer catheter including a hollow tube and an integral or attached fitting at one end of the tube. Comprising the placement unit is connection means having a bore therethrough and including means for mating with the fitting to provide a connection therewith. When this connection is made, the bore is adapted to be aligned with the lumen of the tube. A protective sheath, preferably flexible, is secured to the connection means and includes means in its periphery for allowing insertion of the needle therethrough and then into the bore and the lumen of the introducer catheter. A length of flexible, hollow tubing, serving as the catheter, is movably positioned within and enclosed by the sheath. In use, the connection means is adapted to be connected to the fitting with the needle being insertable through the insertion means in the sheath and through the bore and introducer catheter to provide means for venipuncture. After the needle is withdrawn, the flexible tubing, while enclosed by the sheath, is adapted to be manipulated through the bore and the hollow tube of the introducer catheter and into the patient.

Another aspect of the present invention is a catheter placement system including a catheter placement unit substantially as described above in combination with an introducer catheter including a hollow tube and a fitting at one end thereof. The catheter placement unit is connected to the introducer catheter so that a bore in the connector of the catheter placement unit is aligned with the lumen of the tube of the introducer catheter. This combination further includes an introducer needle inserted through the periphery of the protective sheath and extending through the bore and the lumen of the tube so that the needle tip extends slightly beyond the distal end of the tube. Both the needle and tube are inserted into a patient during use. After the needle is withdrawn from the unit through the sheath, the flexible tubing serving as a catheter, while still enclosed by the sheath, is adapted to be manipulated through the bore and the lumen of the introducer catheter and then into the patient. Preferably, the protective sheath of the catheter placement unit is removable after the catheter is in position in the patient.

A further aspect of the present invention is a method of placing a catheter into a patient. This method includes the step of mating a connector of a catheter placement unit, substantially as described above, to an introducer catheter having a fitting on one end thereof. An introducer needle is inserted through the periphery of the sheath of the catheter placement unit, and through its connector and the hollow tube of the introducer catheter so that the tip of the needle extends slightly beyond the distal end of the tube. Both the needle and the tube are then inserted into a patient. While leaving the tube of the introducer catheter in position in the patient, the needle is withdrawn from the unit. This method further includes manipulating the flexible hollow tubing serving as the catheter, while enclosed by the protective sheath, through the connector and the hollow tube of the introducer catheter and then into the patient. An appropriate connection from, for instance, an intravenous solution administration set or a pressure monitoring device, is then made for utilization of the catheter which has been positioned in the patient.

From the structural standpoint, the catheter placement unit, system and the method of use, are notably different from prior catheter placement devices. For instance, the catheter placement unit of the present invention is a "closed system," inasmuch as the catheter, covered by a protective sheath, is assembled to the introducer catheter-introducer needle combination upon original introduction into the patient. This offers the advantage of having a completely assembled unit without the need for additional connection steps which many of the prior art devices have relied upon. In addition, the catheter placement unit and system of the present invention provides for removal of the needle after the original insertion so that the catheter may function without the needle remaining in the patient. By removing the needle, the concern of cutting or severing the catheter upon movement into the patient's vein is eliminated since the sharp point of the needle is withdrawn before the catheter tubing is slid into place. Thus, the present invention provides, for the first time, a catheter placement unit and device for its introduction into the patient which is essentially a "closed system" in which the introducer needle is withdrawn before the catheter tubing is moved into the patient.

BRIEF DESCRIPTION OF THE DRAWINGS

FIG. 1 is an exploded perspective view of the preferred catheter placement system of the present invention;

FIG. 2 is an enlarged cross-sectional view taken along line 2—2 of FIG. 1;

FIG. 3 is an enlarged plan view of the connector element of the preferred catheter placement unit partially broken away for illustration of the protective sheath connection and the insertion means therein;

FIG. 4 is a view similar to FIG. 3 illustrating an alternate embodiment of the insertion means in the protective sheath;

FIG. 5 is a sectional view of the preferred catheter placement system, shown fully assembled and in condition for insertion into a vein of a patient;

FIG. 6 is a sectional view of the preferred catheter placement unit, illustrated after the needle has been withdrawn, and showing the catheter being manipulated through the connector and introducer catheter into the vein of the patient; and FIG. 7 is a sectional view of the preferred catheter placement unit illustrating the protective sheath being separated from the unit after the catheter has been fed into position in the vein of the patient.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIG. 1, there is illustrated the preferred catheter system 10 of the present invention. This system has three basic components: an introducer catheter 11, an introducer needle 12 and a catheter placement unit 14.

Introducer catheter 11 includes a slender, hollow tube 15 which is open at both ends, with the distal end 16 of the tube being slightly tapered. A hub 18 serves as a fitting at the other, or proximal, end of tube 15. Hub 18 is also hollow so as to communicate with the lumen of tube 15 which extends substantially axially from hub 18.

The hub further includes an internal tapered surface which, together with the hollow portion of the hub, serves as a female fitting connection for reception of catheter placement unit 14. This connection will be described in greater detail hereinafter.

Introducer needle 12 includes a slender barrel 19 with a sharp tip 20 at one of its ends. A handle 21 is at the other end of barrel 19; this handle may also serve as a fitting or connector for possible delivery of solutions through the needle, if desirable. Barrel 19 is preferably a smooth surfaced metal which is adapted to slidably fit inside the lumen of tube 15. It is sized in the particular system of this invention to slide within hollow tube 15 so that needle tip 20, upon assembly, extends slightly beyond distal end 16 of the tube.

Turning to the description of catheter placement unit 14, it includes, generally, a connector 22, an elongated protective sheath 24, and, enclosed by sheath 24 and positioned within, a length of flexible, hollow tubing 25 which is preferably elongated to serve as an extended catheter. At the end of flexible tubing 25 facing away from connector 22 is a fitting 26 to which a subsequent connection may be made to an administration set for delivery of fluids or a pressure monitoring device or the like.

Referring now to FIGS. 2–4, in conjunction with FIG. 1, connector 22 is illustrated in greater detail. This connector includes a substantially cylindrical collar 28 with an internal bore 29 extending therethrough. Bore 29 is stepped at two places to include shoulders 30 and 31. The portion of bore 29 extending outwardly from shoulder 30 has a slight taper 32 in order to receive a compatible tapered retaining ring 34 therein. Retaining ring 34 is also substantially cylindrically shaped and includes a concentric opening 35 therein. Opening 35 of ring 34 when inserted in collar 28 serves as an extension of bore 29. Positioned within opening 35 in a relatively tight fit is a male fitting member 36, which has its male fitting portion 38 extending substantially axially. Male fitting member 36, and in particular the fitting portion 38, is adapted to mate with the internal tapered surface of hub 18 on the introducer catheter to provide the connection therewith. Male fitting member 36 includes a substantially concentric passage 39. Passage 39 is preferably sized to first allow barrel 19 of the introducer needle to slide somewhat snugly therethrough, and then subsequently to provide a similar fit for flexible hollow tubing 25. At the interior end of passage 39 is a somewhat larger cavity 40 which is adapted to receive a portion of fitting 26 after catheter tubing 25 is completely positioned within the patient. Passage 39 is adapted to communicate with bore 29 through cavity 40 so that both the introducer needle and the catheter tubing can be moved through connector 22. The fit of male fitting member 36 in ring 34 is such that it is separable from the ring and collar upon the application of a small amount of manual pressure by the fingers. Ring 34 assists in providing a relatively snug fit of male fitting member 36 to the collar, while allowing ready separability and disengagement when it is time to remove the collar from the male fitting member. This separation will be discussed hereinafter.

In FIGS. 2 and 3 sheath 24 is shown attached to connector 22, and particularly to collar 28. In the embodiment being described, sheath 24 is flexible and is substantially cylindrically shaped in cross-section and is sized to fit inside collar 28 and substantially abut shoulder 31 whereupon it is secured to collar 28 opposite from male fitting member 36. Since both sheath 24 and collar 28 are preferably made of plastic, the attachment may be made by heating sealing; of course, adhesives or other materials or techniques may be employed to secure the sheath to the collar. When secured to the collar, the inside space of sheath 24 is in communication with bore 29 of the collar. This, of course, provides a substantially axial alignment between the sheath and male fitting member so that the flexible tubing can be subsequently moved from inside the sheath through the connector and the male fitting member and then into the patient.

Through the periphery of sheath 24 is a hole 41. This hole is located near the connector and is preferably positioned through the sheath so as to lie inwardly spaced in bore 29 of collar 28. At the point where hole 41 is positioned, sheath 24 is not secured to collar 28 so that the walls of the sheath in the embodiment being described, may be flexed away from the bore of the collar to provide access to hole 41. This hole through the sheath allows insertion of barrel 19 of the introducer needle therethrough and into bore 29 of the collar. In this regard, the hole is sized to accommodate the diameter of the needle barrel and is accordingly relatively small. The hole is preferably located within the confines of the collar to prevent the operator's fingers from inadvertently touching the flexible tubing inside the protective sheath during its insertion into the patient.

Other insertion means may be employed in and through sheath 24 for allowing the insertion of the introducer needle through the connector of the catheter placement unit. For example, an alternate embodiment of this insertion means is illustrated in FIG. 4. Underneath hole 41 is a small disc 42 of elastomeric material, such as rubber which may be adhered to the sheath at the point where the needle puncture is to be made. Disc 42 may include a slit 44 to allow easy penetration of the introducer needle. This type of a puncturable membrane-disc, in addition to allowing needle insertion, also provides a liquid-tight seal after the needle is withdrawn. When using a puncturable membrane of this type, a pre-formed hole in the sheath is optional since the membrane will serve as the path through which the needle will pass.

Catheter placement system 10 is illustrated completely assembled and in the venipuncture position in FIG. 5. Connector 22 of the catheter placement unit has been attached to the introducer catheter by means of male fitting member 36 being inserted into hub 18. Introducer needle barrel 19 has been inserted through hole 41 in sheath 24; it is noted that the sheath is preferably flexed away from the end of bore 29 in collar 28 so as to expose hole 41, and also allow the needle to be inserted concentrically in bore 29 and into passage 39 of the male fitting member. Needle barrel 19 extends completely through hollow tube 15 and projects slightly beyond its distal end. With the introducer needle inserted in this assembly, it is noted that the tip 45 of hollow flexible tubing 25 is spaced a short distance from connector 22. This space is to allow sufficient clearance for the introducer needle to be inserted and then subsequently withdrawn after it performs its venipuncture purpose. It is also noted that protective sheath 24 not only covers the entire length of flexible tubing 25 but also fitting 26 at the end of the flexible tubing. The extreme end 46 of the sheath may be sealed shut, but such a seal is merely optional.

With the components assembled as described, needle tip 20 penetrates the skin of patient P and is introduced into a vein V of the patient. During this venipuncture, hollow tube 15 of the introducer catheter also is introduced into vein V. Once the needle and introducer catheter are in proper position in the vein, the introducer needle is withdrawn by grasping handle 21 and backing the needle out of the introducer catheter and connector of the catheter placement unit through hole 41 in the protective sheath. While the introducer needle is being withdrawn, tube 15 of the introducer catheter remains in position in vein V. When the needle is withdrawn, flexible tubing 25 is inserted, tip 45 first, through connector 22 and on into the lumen of the introducer catheter. This insertion is best seen by referring now to FIG. 6.

With the introducer needle withdrawn, and preferably discarded, the operator grasps sheath 24 with his fingers, designated F, and manipulates flexible tubing 25 into bore 29 of collar 28 and then into passage 39 of male fitting member 36, through hub 18 and hollow tube 15 of the introducer catheter whereupon it exits into vein V of patient P. The flexible, pliant nature of the preferred sheath 24 permits ready movement and manipulation of the flexible tubing within in an expeditious manner. Other non-flexible or semi-flexible sheaths may also be employed as long as the flexible tubing within may be manipulated for insertion into the patient. Moving the flexible tubing through the catheter placement unit while enclosed by the sheath, of course, prevents contamination of the flexible tubing which will be introduced directly into the vein of the patient.

When flexible tubing 25, serving as the catheter, is in position in the patient, fitting 26 at its end is preferably adapted to fit into cavity 40 within male fitting member 36. When the flexible tubing is finally positioned, sheath 24 is no longer required; accordingly, by applying a small amount of pressure, male fitting member 36 is separated from both retaining ring 34 and collar 28. This feature is illustrated in FIG. 7. Inasmuch as sheath 24 is secured to collar 28, this separation effectively removes the sheath and exposes fitting 26 to which a connection may be made to an administration set, pressure monitoring device or the like. At this stage, the catheter placement unit is thus in its operable condition.

Flexible, hollow tubing 25 and hollow tube 15 of the introducer catheter are preferably made from a biocompatible material, such as polytetrafluoroethylene, and are preferably very flexible so that the trauma to the vein or other body tissues of the patient is significantly minimized. Hub 18 of the introducer catheter, and the connector components of the catheter placement unit are preferably plastic. Sheath 24 is preferably a transparent, plastic material generally very pliant and sufficiently thin so as to allow the fingers of the operator to virtually feel the flexible tubing which is enclosed within the sheath.

Thus, there has been provided a catheter placement unit, system and method of use which allows an introducer needle to be withdrawn after venipuncture has been made and which serves as a closed system, i.e., the catheter is attached to the venipuncture instrument when venipuncture is made so that a subsequent connection of the catheter does not have to be made.

What is claimed is:

1. A catheter placement unit for use with an introducer catheter and an introducer needle, said introducer catheter including a hub with an internal tapered surface and a substantially axially extending hollow tube secured at one end to said hub, said catheter placement unit comprising: connector means having an internal bore and a substantially axially extending tapered male portion for mating with the internal tapered surface of said hub, said male portion including an internal passage communicating with said bore; a protective sheath having an end portion inserted into said connector means bore and secured therein on the opposite side from said male portion so that the inside space of said sheath is in communication with said bore, said connector means overlapping the inserted end portion of said sheath; the overlapped end portion of said sheath having means in its periphery for allowing insertion of said needle therethrough and into said bore, passage and tube to provide means for venipuncture, and a length of flexible, hollow tubing movably positioned within and enclosed by said sheath, said tubing including a fitting on its end facing away from said connector means; whereby in use, said male portion of the connector means is mated into said hub, said needle is placed through said sheath and through said bore, passage and tube so that the needle tip extends slightly beyond the distal end of said tube, and after venipuncture is made, said needle is withdrawn, and, while enclosed by said sheath, said tubing is manipulated into said connector means, and through said bore, passage and tube and into the patient.

2. A catheter placement unit as defined in claim 1 wherein said sheath is readily separable from its securement to said connector means.

3. A catheter placement unit as defined in claim 1 wherein said insertion means in said sheath includes a hole through said sheath, said hole adapted to allow said needle to pass therethrough.

4. A catheter placement unit as defined in claim 1 wherein said insertion means in said sheath includes a puncturable membrane on said sheath adapted to allow said needle to pass therethrough and to provide a liquid-tight seal when said needle is withdrawn.

5. A catheter placement unit as defined in claim 1 wherein said connector means includes a collar having an internal bore and a male fitting member positioned in one end of said bore so that its male fitting portion extends therefrom, said sheath secured around said bore at its other end so that said sheath and said male fitting member are substantially in axial alignment.

6. A catheter placement unit as defined in claim 5 wherein said collar and said male fitting member are separable so that said sheath is removable with said collar after said tubing is in position during use.

7. A catheter placement unit for use with an introducer catheter and an introducer needle, said introducer catheter including a hollow tube and a fitting at one end of said tube, said placement unit comprising: connection means having an internal bore and including means for mating with said fitting to provide a connection, said bore adapted to be axially aligned with the lumen of said tube when said connection is made; a protective sheath having an end portion inserted into said connection means bore and secured therein, said connection means overlapping the inserted end portion of said sheath; and the overlapped end portion of said sheath including means in its periphery for allowing insertion of said needle therethrough and into said bore; and a length of flexible, hollow tubing movably positioned within and enclosed by said sheath; whereby, in use, said connection means is adapted to be connected to said fitting with said needle being insertable through said insertion means in said sheath and through said bore and said hollow tube to provide means for venipuncture, and after said needle is withdrawn, said flexible tubing, while enclosed by said sheath, is adapted to be manipulated through said bore and said hollow tube and into the patient.

8. A catheter placement unit as defined in claims 1 or 7 wherein said protective sheath is flexible.

9. A catheter placement unit for use with an introducer catheter and an introducer needle, said introducer catheter including a hub with an internal tapered surface and a substantially axially extending hollow tube secured at one end to said hub, said catheter placement unit comprising: a connector including a collar having an internal bore and having a male fitting member inserted in one end of said bore so that its male fitting portion extends substantially axially therefrom for mating with the internal tapered surface of said introducer catheter hub, said male fitting member including an internal passage communicating with said bore, said fitting member being separable from said collar; an elongated flexible sheath having an end portion inserted into said collar bore and secured therein at the end of the collar opposite from said male fitting member so that said sheath and said male fitting member are substantially in axial alignment, said collar overlapping the inserted end portion of said sheath; and the overlapped end portion of said sheath having a hole through its periphery for allowing insertion of said needle into and through said bore, passage and tube to provide means for venipuncture; and an elongated length of flexible, hollow tubing movably positioned within and enclosed by said sheath, said tubing including a fitting on its end facing away from said connector; whereby said introducer catheter, needle and catheter placement unit are adapted to be in assembled condition during venipuncture, and thereafter, said needle is withdrawable, and said flexible tubing is adapted to be manipulated through said bore, passage and tube into the patient, with said collar being separable from said male fitting member to remove said sheath from said unit after said tubing is in position in the patient.

10. A catheter placement system comprising: an introducer catheter including a hollow tube and a fitting at one of its ends; a catheter placement unit including connection means having an internal bore and means for mating with said fitting to provide a connection, said bore being in substantial axial alignment with the lumen of said tube, said unit including a protective sheath having an end portion inserted into said connection means and secured therein, said connection means overlapping the inserted end portion of said sheath; the overlapped end portion of said sheath having means in its periphery for allowing insertion of a needle therethrough, and a length of flexible, hollow tubing movably positioned within and enclosed by said sheath; an introducer needle inserted through said insertion means in said sheath and through said bore and said hollow tube so that the needle tip extends slightly beyond the distal end of said tube, whereby said needle and hollow tube are insertable into a patient during use, said needle adapted to be withdrawn through said insertion means in said sheath, and said flexible tubing, while enclosed by said sheath, is adapted to be manipulated through said bore and said hollow tube and into said patient.

11. A catheter placement system as defined in claim 10 wherein said sheath is readily separable from its securement to said connection means.

12. A catheter placement system as defined in claim 10 wherein said insertion means in said sheath includes a hole therethrough.

13. A catheter placement system as defined in claim 10 wherein said protective sheath is flexible.

14. A method of placing a catheter into a patient comprising the steps of: mating a connector of a catheter placement unit to a fitting on an introducer catheter having a hollow tube extending from said fitting, said placement unit including:

a protective sheath
  having an end portion inserted into said connector and secured therein, said connector overlapping the inserted end portion of said sheath; the overlapped end portion of said sheath having an insertion means in its periphery; and, a length of flexible, hollow tubing serving as a catheter movably positioned within and enclosed by said sheath;

inserting a needle through said insertion means in the periphery of said sheath and through said connector and into the lumen of said tube so that the tip of said needle extends slightly beyond the distal end of said tube;

inserting said needle and said tube into a patient; withdrawing said needle from said unit and leaving said tube in position in said patient; manipulating said flexible hollow tubing, while enclosed by said sheath, first into and through said connector and said hollow tube and into said patient.

15. A method as defined in claim 14 which further includes the step of removing said sheath from said unit after said flexible tubing is positioned in said patient.

* * * * *